United States Patent [19]

Osbond et al.

[11] Patent Number: 4,890,494

[45] Date of Patent: Jan. 2, 1990

[54] ATMOSPHERIC SENSOR

[75] Inventors: Paul C. Osbond, Northampton, Great Britain; Roger W. Whatmore, Milton Keynes; John P. Auton, Cambridge, both of England

[73] Assignee: Plessey Overseas Limited, Ilford, England

[21] Appl. No.: 196,786

[22] Filed: May 17, 1988

Related U.S. Application Data

[63] Continuation of Ser. No. 657,586, Oct. 4, 1984, abandoned.

[30] Foreign Application Priority Data

Oct. 8, 1983 [GB] United Kingdom ................. 8326982

[51] Int. Cl.<sup>4</sup> ...................... G01N 25/64; G01W 1/02
[52] U.S. Cl. .......................................... 73/338; 73/73
[58] Field of Search ................ 73/29, 171, 27 R, 338, 73/336.5, 336, 73, 613, 338.6; 338/34, 35, 295; 29/595, 612, 610 R, 611, 854

[56] References Cited

U.S. PATENT DOCUMENTS

| | | | |
|---|---|---|---|
| 2,638,783 | 5/1953 | Rittner et al. | 73/29 |
| 2,702,471 | 2/1955 | Vonnegut | 73/29 |
| 2,727,968 | 12/1955 | Rittner et al. | 73/29 |
| 3,517,900 | 6/1970 | Roussel | 73/336.5 X |
| 3,630,084 | 12/1971 | McBride, Jr. et al. | |
| 3,775,843 | 12/1973 | Wendt, Jr. et al. | |
| 3,868,492 | 2/1975 | Taylor | 73/336.5 X |
| 3,886,797 | 6/1975 | Bauer | |
| 3,945,217 | 3/1976 | Bashark | 73/336.5 X |
| 4,101,454 | 7/1978 | Kulwicki et al. | |
| 4,121,088 | 10/1978 | Doremus et al. | 338/295 X |
| 4,254,070 | 3/1981 | Yodogawa et al. | 29/612 X |
| 4,280,114 | 7/1981 | Del Vecchio et al. | 29/610 SG X |
| 4,303,613 | 12/1981 | Yasuda et al. | |
| 4,305,280 | 12/1981 | Vonnegut et al. | 73/171 |
| 4,328,478 | 5/1982 | Murata et al. | 338/35 |
| 4,399,687 | 8/1983 | Collins | |
| 4,485,369 | 11/1984 | Ushida | 338/34 |
| 4,497,701 | 2/1985 | Murata et al. | 73/336.5 X |

FOREIGN PATENT DOCUMENTS

| | | |
|---|---|---|
| 0021225 | 1/1981 | European Pat. Off. |
| 864845 | 4/1961 | United Kingdom . |
| 1097915 | 1/1968 | United Kingdom . |
| 1121522 | 7/1968 | United Kingdom . |
| 1243095 | 8/1971 | United Kingdom . |
| 1288539 | 9/1972 | United Kingdom . |
| 1460746 | 2/1977 | United Kingdom . |
| 1479004 | 7/1977 | United Kingdom . |

OTHER PUBLICATIONS

Elektronik, Lexikon, 2nd Edition, Stuttgart 1982, pp. 305–306, with translation.

Primary Examiner—Daniel M. Yasich
Attorney, Agent, or Firm—Fleit, Jacobson, Cohn, Price, Holman & Stern

[57] ABSTRACT

A device for measuring the liquid content of a gas, as for example measuring the liquid water content in the atmosphere. The device employs a probe fabricated in part from a material which is thermally self-stabilizing and which preferably has a positive temperature coefficient. In use the probe is electrically heated and disposed in a flowing gas or is adapted for movement through a static gas so that droplets of liquid are deposited on the surface of the probe. Means is provided for detecting a change in the electrical resistance of the probe in response to a change in the heat loss rate due to the integrated evaporation of droplets of liquid from the surface of the probe. The temperature of the gas, the degree of relative movement between the probe and the gas, and the gas pressure are also sensed so that when their measurements are processed with a measurement dependent on the change in the electrical resistance of the probe a measurement is obtained of the liquid droplet content in the gas. A particular application for the device is that of measuring the liquid water contents in the air flowing around helicopters and other aircraft, so that the crew can be given warning when they are flying into icing conditions.

20 Claims, 5 Drawing Sheets

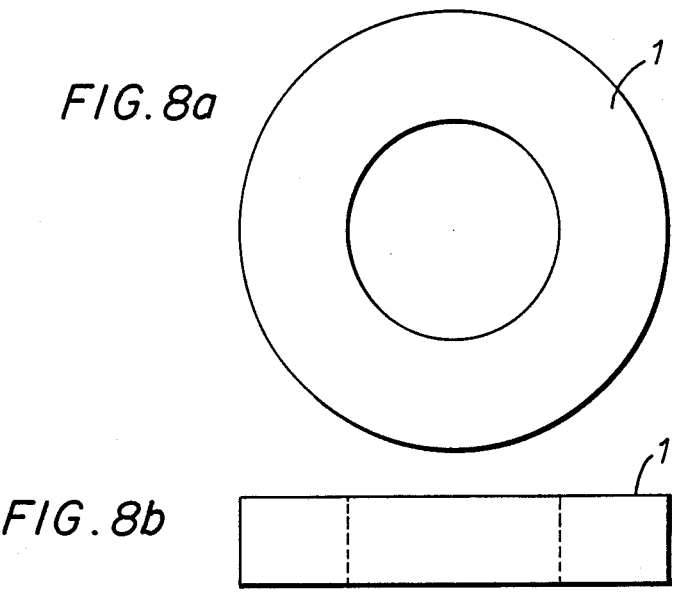
FIG.8a
FIG.8b
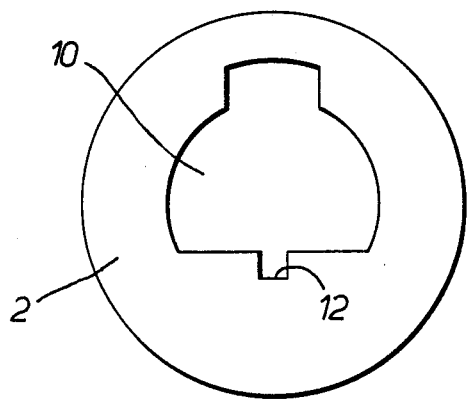
FIG.9

ATMOSPHERIC SENSOR

This application is a continuation of application Ser. No. 657,586, filed Oct. 4, 1984, now abandoned.

BACKGROUND OF THE INVENTION

The present invention relates to a device for measuring the liquid content of a gas, and in one aspect to a device for measuring the liquid water content (LWC) in the atmosphere around aircraft, such as helicopters.

Helicopters are particularly susceptible to the build up of ice on their rotor blades and engine air intakes when operating under cold, damp conditions both because of the increase in the weight of the aircraft and because of the rapid loss of lifting efficiency due to the ice layers that build up on the aerofoils. There is, therefore, a need for a device to measure the LWC in the atmosphere around an operational helicopter so that the crew can be given warning when they are flying into icing conditions.

Various techniques, including both optical and platinum-wire measurements, are capable of determining the atmospheric LWC but most of these are complex and require a considerable amount of electronics for control.

SUMMARY OF THE INVENTION

According to the present invention there is provided a device for measuring the liquid content of a gas, including a probe comprising a material which is thermally self-stabilising and means for detecting a change in the electrical resistance of the probe in response to a change in the heat loss rate due to the evaporation of droplets of liquid from the surface of the material.

Essentially the device utilises the relatively large cooling effect due to the evaporation of droplets of liquid deposited on the surface of the thermally self-stabilising material from an impinging gas stream, compared with the cooling due to convection, conduction and radiation. The gas may be a flowing gas or a static gas but there must be relative movement between the probe and the gas for the measurement of liquid content to take place.

In one embodiment the probe comprises a material having a positive temperature coefficient of resistance (PTCR), means being provided for measuring the current drawn by the probe, means for measuring relative movement between the gas and probe, the gas temperature and the gas pressure and means for processing the measurements to obtain a measurement of the liquid content of the gas. Advantageously the probe comprises a material which is a doped barium titanate ($BaTiO_3$) semiconductor ceramic.

In one embodiment of the present invention the electrical resistivity p of the thermally self-stabilising material at a temperature $\theta$ above the Curie temperature $\theta_N$ conforms to the equation:

$$P = P_o \exp(n_2(\theta - \theta_N))$$

where $n_2$, known as the temperature coefficient, defines the fractional rise in resistivity per degree centigrade above the Curie temperature $\theta_N$. The material is chosen to have a Curie temperature $\theta_N$ above 50° C. and the temperature coefficient $n_2$ is greater than $0.10° C.^{-1}$.

Advantageously the probe is substantially cylindrical in shape and is fabricated from at least one ceramic toroid manufactured from the thermally self-stabilising material. Conveniently the probe is fabricated from a number of ceramic toroids wired electrically in parallel and stacked on top of one another to form a cylinder.

An embodiment of the present invention has the ceramic toroids stacked with interleaving electrically conductive shims between adjacent pairs of toroids. The shims are shaped to allow two electrically conductive elements to extend through the central portion of the stack, each element making electrical contact with a respective major face of each toroid, the major faces of the toroids being coated with an electrically conductive material. Advantageously when the probe is assembled it is coated with a polymer to protect the probe from the environment in which it is to be used.

According to one aspect of the present invention there is provided a probe for use in a device for measuring the liquid content of a gas, the probe comprising a material having a positive coefficient of resistance, the material being in the shape of a toroid having a wall thickness of at least 0.2 mm.

The device and probe can be designed for the measurement of the concentration of any liquid in droplet form in either a flowing gas or a static gas. In the static case movement of the device through the gas is required for the measurement.

In a preferred embodiment of the invention the device and probe are designed for monitoring the liquid water content (LWC) in the atmosphere around an aircraft.

BRIEF DESCRIPTION OF THE DRAWINGS

The present invention will be described further by way of example with reference to the accompanying drawings wherein:

FIGS. 8a and 8b are plan and elevational views, respectively, which illustrate the shape of a ceramic toroid, a number of which are assembled together in the probe of FIG. 6;

FIG. 9 is a plan view of a copper disc, a number of which are positioned between adjacent ceramic toroids in the probe of FIG. 6;

FIG. 12 is a schematic illustration of a probe of the invention being used in conjunction with a carburetor of an internal combustion engine;

FIG. 13 is a schematic illustration of a probe of the invention being used in conjunction with an air-water atmosphere flow adjacent an aircraft and FIG. 14 is a schematic diagram illustrating a liquid droplet measuring system utilizing a probe of the invention.

DESCRIPTION OF A PREFERRED EMBODIMENT

Figure 1:
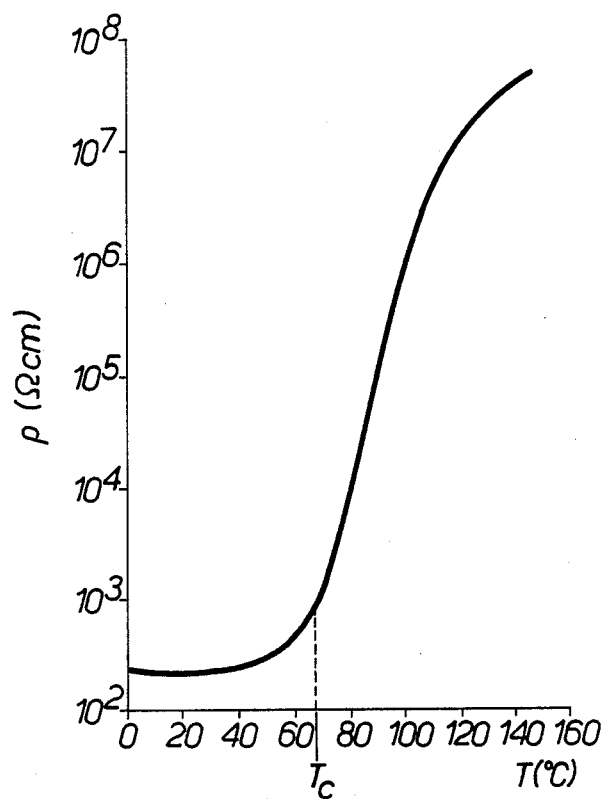
FIG. 1 is a graph showing the resistance of a doped barium titanate ceramic as a function of temperature.

The embodiment of the present invention described below with reference to the drawings makes use of a probe p (FIGS. 6 and 14) the operation of which is dependent on the electrical properties of a suitable positive temperature coefficient of resistance (PTCR) material. Certain doped barium titanate semiconducting ceramics are particularly suitable in this respect. The electrical properties of doped barium titanate can be determined by the concentration of the dopants and the particular dopants used. For example, FIG. 1 shows the resistance of a cer with the composition $(Ba_{0.825}Sr_{0.175})_{0.9965}La_{0.0035}Ti_{1.013}O_3$ as a function of temperature. The use of Sr reduces Tc from 125° C. to the temperature required while the presence of the La makes the material semiconducting. These ceramics are well known and are available commercially. Their preparation will not be the subject of further discussion in this specification.

These ceramics under certain operating conditions are thermally self-stabilising materials.

When suitable electrical contacts are made to the ceramic material and a potential difference is applied, the initial current at room temperature is large as the resistivity of the material is low. Any heat lost at the surface of the ceramic material is equal to the electrical power input at constant temperature. If the potential difference is sufficiently high, the joule heating effect raises the temperature of the ceramic material to above $T_c$ in FIG. 1 where a rapid increase in resistance reduces the current and the power dissipated. At a temperature above $T_c$ a small change in ceramic temperature will give rise to a large change in resistance, and to a large change in dissipated heat. Therefore, large changes in heat lost at the ceramic surface can be tolerated with only small changes in ceramic temperature. Any increase or decrease in the heat dissipation from the surface of the ceramic material causes a corresponding increase or decrease in the current flowing through the material and hence a change in the power dissipated. Under these conditions, the ceramic material behaves as a thermally self-stabilising material, tending to stabilise at a temperature just above $T_c$. The temperature at which stabilisation occurs is dependent on the potential difference and the gradient of the curve above $T_c$ in FIG. 1. The higher the value of the gradient the more closely controlled the stabilisation temperature will be. At a constant voltage the electrical current through the ceramic material is closely related to and therefore a measure of the ambient conditions at the surface of the ceramic material.

As will be described below the probe p comprising the ceramic material can be utilised in a device which is designed and fabricated to measure the liquid droplet content of a gas, and in the case of a wet gas, the water in droplet form. The probe p will hereinafter for the purpose of this description be referred to as a liquid droplet/gas probe (LDGP).

The way such a ceramic material is configured in the LDGP makes use of the relatively large cooling effect due to the evaporation of droplets of liquid deposited on its surface from a gas stream flowing over it when compared with the cooling due to radiation and convection and conduction due to the gas alone.

A good model of the physical characteristics of a PTCR ceramic such as that shown in FIG. 1 is given by equations relating the electrical resistivity and temperature of the material: ps $$p=p_o\cdot\exp(-n_1(\theta-\theta_N))\quad \theta\leq\theta_N \qquad (1)\,\text{ps}$$
$$p=p_o\cdot\exp(n_2(\theta-\theta_N))\quad \theta>\theta_N \qquad (2)$$

Figure 2:
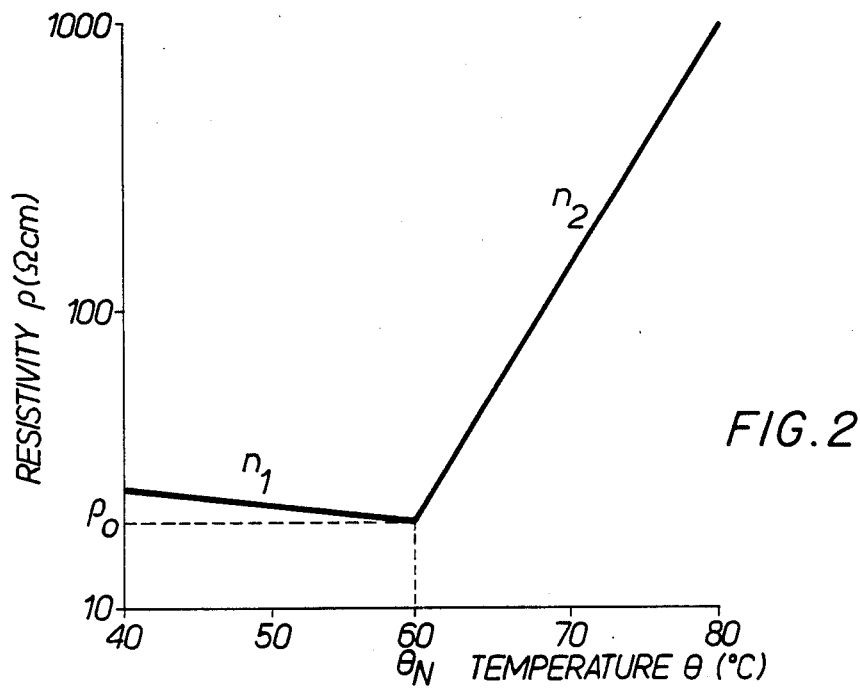
FIG. 2 is a graph illustrating the variation in electrical resistivity of the doped barium titanate ceramic with temperature on which a thermal performance model is based.

At a characteristic temperature $\theta_N$, the electrical resistivity p is taken to have a minimum value po, as shown in FIG. 2. Below that temperature, the resistivity rises $n_1\%$ per ° C. as temperature falls. Above that temperature, the resistivity rises $n_2\%$ per ° C. as temperature rises. The Curie temperature, which is taken as the temperature at which the rate of change of the resistivity gradient is a maximum, is close to $\theta_N$.

The selection of a suitable PTCR ceramic for application of the probe p as an ice probe involves the specification of attainable values of $p_o$, $\theta_N$, $n_1$ and $n_2$ (and tolerances in those values) which result in acceptable thermal performance of the probe.

By the inclusion of insolvent impurities in PTCR barium titanate ceramic the Curie temperature can be modified to suit the particular requirements. For a material to be suitable, the generated power has to vary sufficiently widely across the operating range to enable changes in the ambient atmospheric conditions to be sensitively discriminated.

Figure 3:
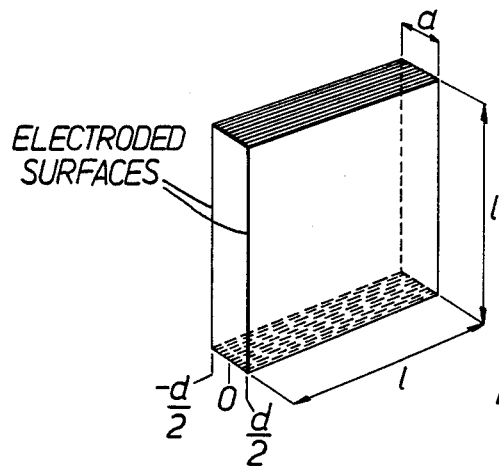
FIG. 3 illustrates a doped barium titanate ceramic slab used in the thermal model.

Considering a slab of PTCR ceramic with electrodes on the faces as shown in FIG. 3 the heat is removed by convection from the two faces $p\times p$ at $\pm d/2$. Assuming the electrodes are subject to 200V/cm, $\theta_N=60°$ C., $p_o=20\,\Omega\text{cm}$, $n_1=10^{-2}$ ° C.$^{-1}$, $n_2=0.2$ ° C$^{-1}$, ambient temperature $\theta_o=20°$ C. and the thermal resistivity of the ceramic $k=0.03\,\text{Wcm}^{-1}$ ° C.$^{-1}$, it is found that the slab temperature and power generated in the slab rise to a maximum as the thickness is increased, and are constant above a saturation thickness of d/2 32 $\pm 0.2$ mm. The saturation thickness is based on a practical maximum surface heat transfer coefficient of $\alpha \approx 1\,\text{Wcm}^{-2}$° C.$^{-1}$. The effect of using lower values of $\alpha$ is to flatten the internal temperature in the slab and to raise the wall temperature.

For a typical constant value of $\alpha$, the current reaches a maximum at a certain voltage. In the lower voltage range, the slab has a temperature less than $\theta_N$. Above the critical voltage however, the temperature exceeds $\theta_N$. For a constant voltage applied to the slab, the current drawn varies with the surrounding conditions. Provided the voltage exceeds the turning voltage for the maximum value of $\alpha$, the variation of the current with $\alpha$ is substantial, and depends on the value of $n_2$ which is the resistivity gradient of the selected PTCR ceramic.

Figure 4:
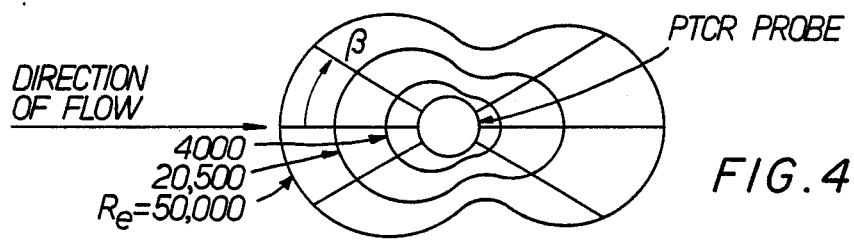
FIG. 4 illustrates the circumferential variation of the Nusset number Nu surrounding a cylindrical probe for a range of Reynolds number Re.
Figure 5:
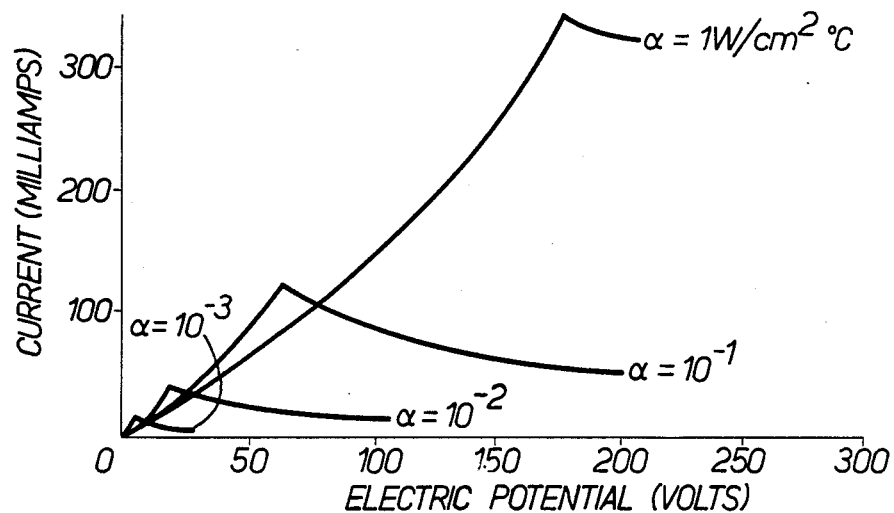
FIG. 5 illustrates current voltage characteristics for different values of surface heat transfer rates ($\alpha$) for the probe.

By making the dimension d/2 very small, the slab can be considered as an elemental strip of a hollow cylindrical probe p being cooled from only one side. It can then be used to model the behaviour of the probe p under varying conditions. For applications with helicopters, the probe p is required to operate at relative air velocities between 20 ms$^{-1}$ and 90 ms$^{-1}$, and these velocities correspond to Reynolds numbers between 4,000 and 20,000. At these Reynolds numbers, the heat transfer coefficient $\alpha$ is not constant around the periphery of the probe p as can be seen in FIG. 4. Corresponding curves can therefore be obtained for the current drawn by the probe p (running dry) by integrating the family of current-voltage curves in FIG. 5.

In dry air at 90 m/s and 5° C. the Reynolds Number Re =21,000 and the mean Nusselt Number Nu=105 corresponding to the mean surface heat transfer co-efficient =0.06 Wcm$^{-2}$ ° C.$^{1}$. Assuming a 0.2 mm wall thickness, the local rates of heat loss and heat transfer coefficient at certain angular positions (for the PTCR material discussed above) are approximately:

| $\beta$ Angular Position | PTC Temperature °C. Surface | Core | Heat Loss w/cm$^2$ | $\alpha$ W/cm$^2$ °C. |
|---|---|---|---|---|
| 0° | 68 | 70 | 9.0 | 1.06 × 10$^{-1}$ |
| 30° | 69 | 71 | 8.0 | 9.7 × 10$^{-2}$ |
| 90° | 72 | 73 | 3.5 | 4.0 × 10$^{-2}$ |

The surface temperature only falls to the characteristic temperature $\theta_N = 60°$ C. if $\alpha > 0.5$ Wcm$^{-2}$° C.$^{-1}$. However, since the maximum power loss at the 0° position on the probe p even at the highest air droplet concentration (90 ms$^{-1}$, 1.6 g/m$^3$) is 13.0 Wcm$^{-2}$ in addition to the 9.0 Wcm$^{-2}$ heat transfer rate, the surface temperature of the probe p does not fall to the characteristic temperature in practice.

When particles or droplets of liquid land on the surface of the probe p, the device is cooled partly by heat convection and partly by mass convection as the drops evaporate.

For a single drop of mean size 20$\mu$, the region of the probe p where the drop lands gives up heat rapidly so that the drop is heated through. A drop of this size responds at such a rate that the outside is in equilibrium with the probe wall in about 3 milliseconds. Assuming 1.6 g/m$^3$ moisture content and 90 ms$^{-1}$ air velocity, the average period before the next drop will land on the same point can be calculated statistically as being 0.3 seconds. The drop surface therefore has to be hot enough to cause it to evaporate into the ambient airstream within that period, if the moisture layer is not to build up and cover the probe with a layer of liquid.

If the probe p is made with a thicker wall (i.e. more than 0.2 mm), there is a response of the inside of the probe which alters conditions on the outer surface, and this will follow in a period which is about 1 second after a change in probe environment. The thermal mass of the probe p is, of course, large compared with that of impinging water drops, so that the temporary localised temperature depression in the region where the drop lands can be ignored.

The theoretical study described above indicates that the PTCR material required requires a value of $\theta_N$ above 50° C. and the temperature coefficient n$_2$ should be greater than 0.10° C.$^{-1}$. The dimensions of the device are not critical provided that the surface area exposed to the gas flow is known. Probes p which have been fabricated and tested in wind tunnels and on operational helicopters have been composed of a hollow cylinder of ceramic which is 8.0 mm in diameter and 40 mm in length. The cylinder is divided into a number of sections (or toroids) which are connected electrically in parallel so as to reduce the operating voltage. It has been found experimentally that ceramics with the composition $(Ba_{0.825}Sr_{0.175})_{1-y}La_yTi_{1+\delta}O_3$ (with y=0.0035 and $\delta$=0.013) and containing a second phase addition of 0.1 mole % Li$_2$O$_3$, 0.15 mole % Al$_2$O$_3$ and 0.5 mole % SiO$_2$, exhibit the required electrical properties with $\theta_N$ and n$_2$ equal to 70° C. and 0.17° C.$^{-1}$ respectively. Other materials which may also be suitable in this application are Cr-doped V$_2$O$_3$ ceramics which exhibit a PTCR behaviour when they undergo a metal-insulator transition at a temperature determined by the concentration of Cr. Fabrication of the ceramic probe is described in detail below.

In order to calculate the liquid content of a gas, the power Q (watts) required to maintain the cylinder at its operational temperature, the true gas velocity V(ms$^{-1}$), the static gas temperature T$_{st}$(K) and the static gas pressure P$_{st}$ (N.m$^{-2}$) are required. Referring to the schematic diagram in FIG. 14, this may be accomplished by connecting the probe P to a power supply 20, and measuring the power Q with a current measuring device 22. The gas or air velocity can be measured with a pitot tube 24 the gas or air temperature determined by a thermistor 26 and the gas or air pressure determined by a pressure measuring device 28. The measuring devices 22 and 28, pitot tube 24 and thermistor 26 all feed signals to a liquid droplet measuring device 30. The liquid content of a gas can be obtained by subtracting the convective power from the measured power; the convective power is a once-only measurement and the constants derived are then fixed for a particular installation. Measurements are required of probe power over a range of airspeeds and temperatures in dry air.

If the surface temperature T$_{sf}$ (K) of the probe is known then T$_f$(K), the droplet film temperature can be taken as the arithmetic mean:

$$T_f = (T_{sf} + T_{st})/2 \quad (3)$$

and the dynamic viscosity of air $\mu_f$ at T$_f$ is given by the formula:

$$\mu_f = \frac{1.5 \times 10^{-6} \times T_f^{1.5}}{(T_f + 118)} \text{ kg/ms} \quad (4)$$

knowing the thermal conductivity k$_f$ of air at T$_f$ and the density of air at T$_{st}$, Nu and Re can be calculated to be $$Nu = hD/K_f \quad (5)$$

$$= \frac{Q.D.}{A_s (T_{sf} - T_{st})K_f} \quad (6)$$

$$\text{and } Re = \frac{P_a VD}{\mu_f} \quad (7)$$

where h, the convective heat transfer coefficient is calculated by the formula:

$$h = \frac{Q}{A_s \cdot (T_{sf} - T_{st})} \quad (8)$$

A$_s$ is the probe surface area, D is the probe diameter and P$_a$(kgm$^{-3}$) is the density of air at T$_{st}$. The gradient N and intercept B of a graph of log Nu against log Re can then be used to calculate the LWC (denoted M). The total power applied to the probe p equals the power lost by convection plus that required to evaporate the water, $$Q = h \cdot A_s(T_{sf} - T_{st}) + EA_p VM(L_e + C_w(T_{sf} - T_{st})) \quad (9)$$

where
E = overall water droplet catch efficiency for the probe p
$A_p$ = probe projected area
$L_e$ = latent heat of evaporation of water = $2.36 \times 10^6$ J kg$^{-1}$
$C_w$ = specific heat of water = $4.2 \times 10^3$ J kg$^{-1}$ °C.$^{-1}$
Hence $$M = \frac{Q - h \cdot A_s(T_{sf} - T_{st})}{EA_p V \times (L_e + C_w(T_{sf} - T_{st}))} \text{ Kgm}^{-3} \quad (10)$$

It can be shown that $$h = \frac{BK_f}{D} \cdot \frac{(p_a V D)^N}{\mu_f} \quad (11)$$

and $$E = \frac{K}{K + H_e} \quad (12)$$

where $H_e$ is the efficiency parameter $$= \pi/2 + 0.121 R_d^{0.6} + 0.754 \times 10^{-4} R_d^{1.38} \quad (13)$$

$R_d$ is the droplet Reynolds Number $$K = \text{droplet inertia parameter} = \frac{1/9 \, p_w d_2 v}{\mu_a D} \quad (14)$$

($d_2$ = mean droplet diameter, $p_w$ is the density of water and $\mu_a$ is the viscosity of air). Hence substitution of equations 11 and 12 into equation 10 gives the value of M i.e. the mass of water in Kg per cubic meter of gas. The only variables for any one installation are Q, V, $T_{st}$ and $P_{st}$ ($P_{st} = p_a \cdot T_{st} 287.1$). In the case of sensing the LWC around an operational helicopter, the Q is derived directly from the current drawn by the probe p and the other variables from the other helicopter instruments. A suitable computation of LWC can then be performed using an on-board processor such as the device 30 in FIG. 14.

The method for fabricating the probe p is described below and involves (i) plating PTCR material with nickel, (ii) design of components used to make electrical connections to the ceramics, (iii) design of an assembly jig (iv) application of solder (v) grinding the probe and (vi) insulating the internal and external surfaces of the probe. The description which follows applies specifically to semiconducting barium titanate ceramic as the PTCR material, but a similar method could be used with other materials as discussed above.

Figure 6:
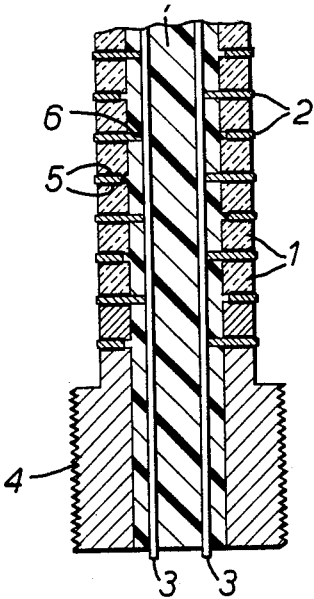
FIG. 6 is a schematic diagram of a probe according to one embodiment of the present invention.
Figure 7:
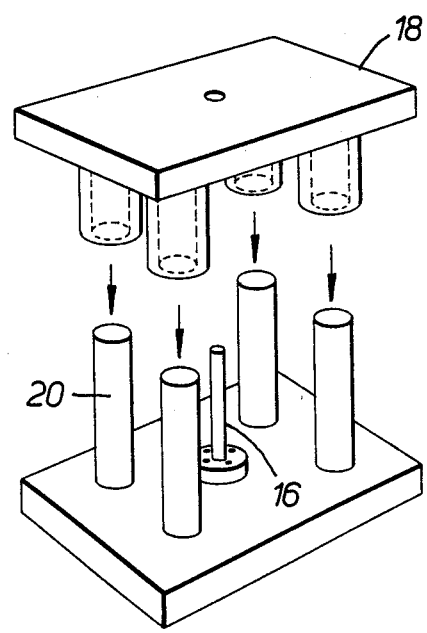
FIG. 7 illustrates a construction jig for assembling a probe like that shown in FIG. 6.

FIG. 6 shows a practical design for the probe p and FIG. 7 demonstrates a jig which is suitable for probe fabrication. Twenty PTCR ceramic toroids 1 as shown in FIG. 8 with the basic composition of $(Ba_{0.825} Sr_{0.175})_{1-y}La_y Ti_{1+\delta}O_3$ (with y = 0.0035 and $\delta$ = 0.013) are plated on their major faces using an electroless nickel plating technique such as has been previously described. The plated ceramics are annealed at 300° C. so as to minimize the contact resistance between the metal and ceramic and the electrodes are then coated with a thin layer of resin-based flux/preservative to prevent further oxidation of the nickel and to allow good solderability.

In order that the operating voltage is kept to minimum, the ceramic toroids have to be connected electrically in parallel. This is achieved using copper discs 2, one of which is shown in FIG. 9, the copper discs are positioned between the toroids 1 shown in FIG. 6. The discs 2 which are also prefluxed before assembly, have a central cut out 10 shown in FIG. 9 which permits them to be placed centrally on a stainless steel post 16 shown in FIG. 7 of the jig. The cut-out 10 includes a narrow slot 12 for a pair of tinned copper wires 3 shown in FIG. 6 to be soldered to, and alternate discs 2 are rotated by 180° with respect to each other so that the wires only make electrical contact to alternate toroid faces.

The complete device, including a threaded copper base 4 is soldered together by using two 5 micron thick foil washers 5 made of 60/40 lead/tin solder (FIG. 6) which are positioned between every plated toroid face and every copper disc 2. The copper base can be of any design which is suitable for securing the device when operating and could be omitted if, for example, the probe p was bonded to its support using a high temperature epoxy. The solder washers 5 allow a consistently uniform layer of solder between surfaces but other methods of applying the solder can be employed if the thickness of deposition is controlled (for example, the deposition of solder alloys by electrolysis). Electrical contact between the copper discs 2 and the tinned copper wires 3 is ensured by placing a small blob of solder paint 6(a suspension of solder particles in a fluid) around the plot 12 through which the wires pass.

Before the assembly is placed in an oven, pressure on the probe p is applied from above using a thick brass plate 18 (FIG. 7) which slides over four guiding rods 20 of the assembly jig. Hence, when the probe p and jig are heated to a temperature above the melting point of the solder (200° C.) the flux is squeezed out from the surfaces and the strength of the solder bonds is optimized.

After the solder has melted and the probe p is cooled and removed from the jig, it can be operated as a liquid content sensor. However, the probe surface is rough and irregular so that the surface area is difficult to calculate. Also, electrical insulation is desirably required on the outside and inside surfaces of the device if it is going to be operated in an environment containing an electrolyte, for example water.

The probe p can be ground on a lathe to a known diameter using a diamond grinding wheel. The inside of the probe p is desirably filled with a high temperature epoxy 7 (FIG. 6); conventional epoxy resins are not suitable since the inside of the probe p can be above 100° C. (depending on the value of $\theta_N$ chosen).

To prevent electrolysis occurring on the surface of the probe p a suitable coating 8 (FIG. 6) has to be applied which will not only resist electrolytes but also has to be resistant to erosion from particles in the atmosphere. However, since the operation of the probe p relies on the cooling effect of droplets impinging on the surface, external coatings will slow the time response of the device. Therefore a durable coating of between 10 and 50 $\mu$m is required if the time response of the probe p is to be kept to about 1 second although thicker coatings are suitable if a device with a time constant of several seconds is permissible. It has been found that polyimide coatings offer the greatest protection against electrolysis and erosion, although devices coated with epoxy resins and other polymers have been tested in simulated conditions and were found to operate satisfactorily.

Nolimid 32, a high purity modified polyimide, was found to be particularly suitable for coating LDGP's because of its mechanical and chemical properties at raised temperatures. The resin is applied to the surface of the probe p in thin layers and each layer is dried at 130° C. for 15 minutes prior to curing at 250° C. for a further 15 minutes. Although the melting point of the Pb/Sn solder is around 200° C., the high temperature epoxy 7 resin which fills the centre of the probe p enables the latter to withstand this high curing temperature without affecting the mechanical strength of the device.

Figure 10:
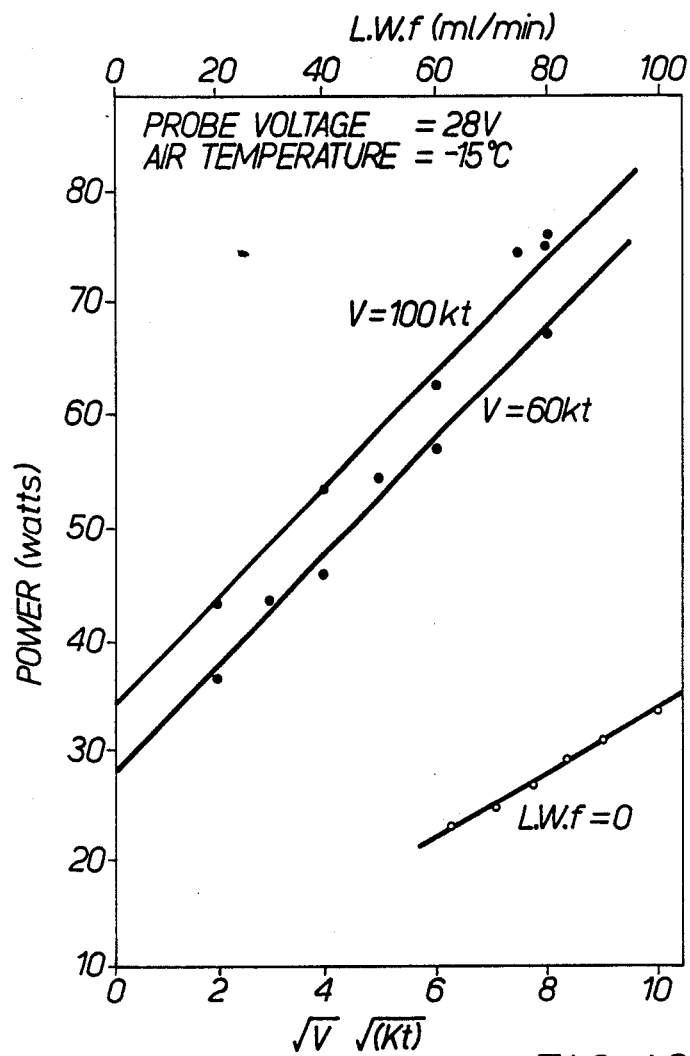
FIG. 10 is a graph illustrating the power output from a probe according to one embodiment of the present invention, the power output being shown as a function of liquid water flow rate (LWF) at two constant air velocities (60 knot and 100 knot) and as a function of the square root of the velocity ($\sqrt{v}$) at constant LWF.

Results from tests carried out on a PTCR ceramic LDGP in a wind tunnel are given in FIG. 10. This shows the power drawn by the probe p at constant temperature ($-15°$ C.) for different liquid water flow rates (LWF) and for constant air velocities of 60 and 100 knots. A constant potential of 28 volts was applied to the probe p so that the power drawn is directly proportional to the current flowing. It can be seen that a linear relationship exists between power dissipation and LWF and that the power drawn at constant liquid water flow is proportional to the square root of the air speed. The slight vertical power displacement in this figure between the 60 knot and 100 knot lines is due to the convective term in the heat transfer coefficient. The thermal self-stabilisation of the probe p is demonstrated by the fact that an increase in the the LWC from $Ogm^{-3}$ to 1.5 $gm^{-3}$ at constant air velocity increased the current drawn by the probe by 104% out only decreased the probe temperature by 3.6° C.

The linearity of the curves shown in FIG. 10 means that it is a relatively simple matter to compute the LWC in the atmosphere when the other variables (V, $T_{st}$ and $P_{st}$) are measured.

The primary application of the LDGP is in the measurement of the liquid water droplet content in the atmosphere around helicopters and fixed wing aircraft. This is of particular importance in sensing when the aircraft is flying in icing conditions.

Figure 11:
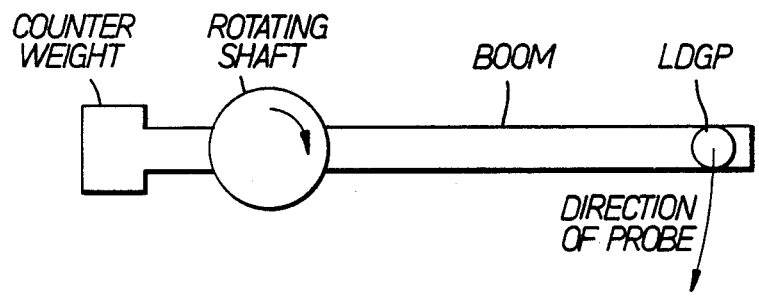
FIG. 11 illustrates a method according to one embodiment of the present invention of measuring the liquid droplet concentration of a static gas.

A LDGP, as described above, could also be used to measure the liquid droplet concentration in a static atmosphere, provided the probe is moved through the gas at a known speed. One method of achieving this is to secure the LDGP on one end of a rotating boom mounted on a rotating shaft (FIG. 11) having a counterweight on an opposite end thereof. By way of example, the LDPG then may be electrically connected to the liquid droplet measuring device 30 in a suitable known manner, not shown in detail. Such a device for example could then give an accurate measurement of the liquid water content of fog and could therefore be used as a warning device on motorways as well as a measurement device for fog irrigation of plants in greenhouses, measurement of liquid droplet entrainment in gases used in chemical processes and measurements of liquid droplet entrainment for the characterising of atomising sprays.

Another possible application of the LDGP is the monitoring of fuel supplied by internal combustion engine carburetors, as illustrated in FIG. 12. The air/fuel mixture from the carburetor would pass over the probe p stabilized at a suitable operating temperature and the power required to maintain the LDGP at a constant temperature could be used to compute the rate at which fuel is injected into the engine. Such a device could be used to optimise the fuel consumption of an engine if the flow of fuel into the carburetor could be adjusted as a result of data from the LDGP.

In all the applications above including the aircraft LWC, the probe p need not be a cylinder but could for example be a small flat plate.

The embodiment of the device described above utilises a probe p comprising a material having a positive temperature coefficient of resistance (PTCR) which is thermally self-stabilising, means being provided for measuring the current drawn by the probe whilst the voltage is kept constant. In other embodiments of the present invention the probe p comprises a material having a negative temperature coefficient of resistance (NTCR), which is thermally self-stabilising, means being provided for measuring the voltage drawn by the probe p whilst the current is kept constant. These other embodiments are however less preferred embodiments. It will also be appreciated that the probe configuration does not have to be cylindrical but it is convenient to employ a cylindrical configuration as it considerably simplifies the mathematical model which is used to measure the water content. In one of the preferred embodiments of the present invention a cylindrical probe p is employed which operates at between approximately 65° C. and 75° C., using a ceramic of semiconducting Barium Strontium Titanate. Such a probe p has been found practical for measuring the liquid water contents in the air flowing around helicopters and other aircraft as illustrated in FIG. 13. For the purpose of the above described embodiments by referring to thermally self-stabilising material is meant one having a Curie temperature $T_c$ characteristic, such that a change in the temperature of the material above $T_c$ gives rise to a relatively large change in resistance as exemplified by FIG. 1 and the corresponding previous discussion herein, thereby enabling the material, when subjected to controlled electrical voltages or currents, to obtain a predetermined temperature above $T_c$ and maintain its temperature close to that predetermined temperature.

We claim:

1. A device for measuring a liquid content of a gas, the device including a probe comprising a sensor formed by ceramic material which is thermally self-stabilising because it has a known resistance/temperature characteristic, the probe ceramic material having an electrical resistance and a heat loss rate at a surface of the ceramic material, the electrical resistance changing in response to the heat loss rate resulting from integrated evaporation of liquid droplets in said gas from the surface of the ceramic material, means for heating the probe to a required temperature, means for detecting a change in the electrical resistance of the probe, in response to a change in the heat loss rate due to the integrated evaporation of liquid droplets in said gas from the surface of the ceramic material, means for maintaining the temperature of the probe substantially constant during operation whereby the change in the electrical resistance indicates a variation in power used to maintain the temperature of the probe substantially constant, and means for processing the variation of power for determining the liquid content of the gas.

2. A device according to claim 1 wherein the ceramic material has a positive temperature coefficient of resistance, and the device further comprises means for measuring a current drawn by the probe to determine the change in electrical resistance of the probe, means for measuring relative movement between the probe and the gas, the temperature of the gas and gas pressure, and means for processing the measurements to obtain a measurement of the liquid content of the gas.

3. A device according to claim 2 wherein the electrical resistivity P of the ceramic material at a temperature $\theta$ above the Curie temperature $\theta_N$ is given by the equation:

$$P = P_o \exp(n_2 (\theta - \theta_N))$$

where $n_2$, known as the temperature coefficient, defines the fractional rise in resistivity per degree centigrade above the Curie temperature $\theta_N$, and wherein the ceramic material is chosen to have a Curie temperature above 50° C. and the temperature coefficient is greater than $0.1020$ C.$^{-1}$.

4. A device according to claim 3 wherein the probe material comprises a doped barium titanate ($BaTiO_3$) semiconductor ceramic.

5. A device according to claim 1 wherein at least a portion of the probe ceramic material is substantially cylindrical in configuration.

6. A device according to claim 5 wherein the probe structure comprises at least one ceramic toroid manufactured from the thermally self-stabilising material.

7. A device according to claim 1 wherein the probe ceramic material has a negative temperature coefficient of resistance and the device further comprises means for measuring a potential difference across the probe while a current is maintained constant, means for measuring relative movement between the probe and the gas, means for measuring gas pressure, and means for processing the measurements to obtain a measurement of the liquid content of the gas.

8. A device for measuring a liquid content of a gas including a probe comprising a sensor formed by ceramic material which is thermally self-stabilising because it has a known resistance/temperature characteristic, the probe ceramic material having an electrical resistance and a heat loss rate at a surface of the ceramic material, the electrical resistance changing in response to the heat loss rate resulting from integrated evaporation of liquid droplets in said gas from the surface of the ceramic material, and means for detecting a change in the electrical resistance of the probe, in response to a change in the heat loss rate due to the integrated evaporation of droplets of liquid from the surface of the ceramic material, the probe including a plurality of substantially cylindrical ceramic toroids of the thermally self-stabilising material, wired electrically in parallel and stacked on top of one another to form a cylinder.

9. A device for measuring a liquid content of a gas including a probe comprising a sensor formed by ceramic material which is thermally self-stabilising because it has a known resistance/temperature characteristic, the probe having an electrical resistance and a heat loss rate at a surface of the ceramic material, the electrical resistance changing in response to the heat loss rate resulting from integrated evaporation of liquid droplets in said gas from the surface of the ceramic material, and means for detecting a change in the electrical resistance of the probe in response to a change in the heat loss rate due to the integrated evaporation of droplets of liquid from the surface of the ceramic material, the probe including a plurality of substantially cylindrical ceramic toroids of the thermally self-stabilising material wired electrically in parallel, and the probe further including interleaving electrically conductive shims between said toroids, said toroids and interleaving shims being stacked on top of one another to form a cylinder.

10. A device according to claim 9, wherein the shims are shaped to allow two electrically conductive elements to extend through the central portion of the stack, each said element making electrical contact with a respective major face of each toroid, the major faces of the toroids being coated with an electrically conductive material.

11. A device for measuring a liquid content of a gas, the device including a probe comprising a sensor formed by ceramic material which is thermally self-stabilising because it has a known resistance/temperature characteristic, the probe ceramic material having a positive temperature coefficient of resistance, an electrical resistance and a heat loss rate at a surface of the ceramic material, the electrical resistance changing in response to the heat loss rate resulting from integrated evaporation of liquid droplets in said gas from the surface of the ceramic material, means for heating the probe to a required temperature, means for detecting a change in the electrical resistance of the probe, in response to a change in the heat loss rate due to the integrated evaporation of liquid droplets in said gas from the surface of the ceramic material, means for maintaining the temperature of the probe substantially constant during operation whereby the change in the electrical resistance indicates a variation in power used to maintain the temperature of the probe substantially constant, means for measuring relative movement between the probe and the gas, the temperature of the gas and gas pressure, and means for processing the variation of power and the measurements for determining the liquid content of the gas.

12. A probe for use in a device for measuring a liquid content of a gas, the probe comprising a sensor formed by ceramic material which is thermally self-stabilising because it has a known resistance/temperature characteristic, the probe ceramic material having an electrical resistance and a heat loss rate at a surface of the ceramic material, the electrical resistance changing in response to the heat loss rate resulting from integrated evaporation of liquid droplets in said gas from the surface of the ceramic material, and the ceramic material having a positive temperature coefficient of resistance.

13. A probe for use in a device for measuring a liquid content of a gas, the probe comprising a sensor formed by ceramic material which is thermally self-stabilising because it has a known resistance/temperature characteristic, the probe ceramic material having an electrical resistance and a heat loss rate at a surface of the ceramic material, the electrical resistance changing in response to the heat loss rate resulting from integrated evaporation of liquid droplets in said gas from the surface of the ceramic material, the probe having a substantially cylindrical shape, and the probe ceramic material also having a positive temperature coefficient of resistance and being formed in the shape of a toroid having a wall thickness of at least 0.2 mm.

14. A probe for use in a device for measuring a liquid content of a gas, the probe comprising a sensor formed by ceramic material which is thermally self-stabilising because it has a known resistance/temperature characteristic and a positive temperature coefficient of resistance, the probe having an electrical resistance and a heat loss rate at a surface of the ceramic material, the electrical resistance changing in response to the heat loss rate resulting from integrated evaporation of liquid droplets in said gas from the surface of the ceramic material, the probe also having a substantially cylindrical shape and having an operating temperature range of between approximately 65° C. and 75° C., and the material being a ceramic of semiconducting Barium Strontium Titanate.

15. A probe for use in a device for measuring a liquid content of a gas, the probe comprising a sensor including a stack of a plurality of toroids of a ceramic material which is thermally self-stabilising because it has a known resistance/temperature characteristic, the probe ceramic material forming the toroids also having a positive temperature coefficient of resistance, and having an electrical resistance and a heat loss rate at a surface of the ceramic material, the electrical resistance changing in response to the heat loss rate resulting from integrated evaporation of liquid droplets in said gas from the surface of the ceramic material, a plurality of interleaving electrically conductive shims between adjacent pairs of toroids, electrically conductive elements extending through a central portion of the stack of toroids and interleaving shims with each said element making electrical contact with an electrically conductive material on a respective major face of each toroid, and a plastic coating on surface portions of the probe to protect the probe from the environment.

16. A method of measuring a liquid content of a gas including the steps of measuring relative velocity between a probe and the gas, the probe comprising a sensor formed by ceramic material which is thermally self-stabilising because it has a known resistance/temperature characteristic, and the probe ceramic material having an electrical resistance and a heat loss rate at a surface of the ceramic material, the electrical resistance changing in response to the heat loss rate resulting from integrated evaporation of liquid droplets in said gas from the surface of the ceramic material, measuring temperature of the gas, measuring pressure of the gas, detecting a change in the electrical resistance of the probe, in response to a change in the heat loss rate due to the integrated evaporation of liquid droplets in said gas from the surface of the thermally self-stabilising ceramic material, providing a measurement dependent on the change in the electrical resistance of the probe, and processing the measurement to obtain a measurement of the liquid content of the gas.

17. A method of measuring the liquid content of a gas according to claim 16 the gas is substantially air and the liquid is substantially water.

18. A method of measuring the liquid content of a gas according to claim 16 wherein the probe moves through substantially static gas.

19. A method of measuring the liquid content of a gas according to claim 15 in the probe is mounted in an air/fuel mixture stream from an internal combustion engine carburetor so as to monitor the quantity of fuel supplied by the carburetor.

20. A method of measuring a liquid content of a gas including the steps of measuring relative velocity between a probe and the gas, the probe comprising a sensor formed by ceramic material which is thermally self-stabilising because it has a known resistance/temperature characteristic, and the probe ceramic material having an electrical resistance and a heat loss rate at a surface of the ceramic material, the electrical resistance changing in response to the heat loss rate resulting from integrated evaporation of liquid droplets in said gas from the surface of the ceramic material, measuring temperature of the gas, measuring pressure of the gas, detecting a change in the electrical resistance of the probe in response to a change in the heat loss rate due to the integrated evaporation of droplets of liquid from the surface of the thermally self-stabilising ceramic material, providing a measurement dependent on the change in the electrical resistance of the probe, and processing the measurement to obtain a measurement of the liquid content of the gas, wherein the temperature of the probe is maintained substantially constant and the measurement provided to measure the liquid content of the gas is the power dissipated to maintain the temperature of the probe substantially constant.

* * * * *